United States Patent [19]

Robert et al.

[11] 4,179,217

[45] Dec. 18, 1979

[54] DYNAMIC PHOTOELASTICIMETER WITH ROTATING BIREFRINGENT ELEMENT

[75] Inventors: André J. Robert, Paris; Jean C. Filippini, Grenoble; Michel Ferré, Palaiseau, all of France

[73] Assignee: Etat Francais as represented by the Delegue General pour l'armement, Paris, France

[21] Appl. No.: 877,758

[22] Filed: Feb. 14, 1978

[30] Foreign Application Priority Data

Feb. 21, 1977 [FR] France .................................. 77 04871

[51] Int. Cl.$^2$ ........................... G01J 4/04; G01L 1/24
[52] U.S. Cl. ...................................... 356/33; 356/365
[58] Field of Search ................... 356/33, 34, 114, 115, 356/116, 117, 364, 365, 366, 367, 368

[56] References Cited

U.S. PATENT DOCUMENTS

| | | | |
|---|---|---|---|
| 3,738,755 | 6/1973 | Chaney et al. | 356/117 |
| 3,740,151 | 6/1973 | Chaney et al. | 356/117 |
| 3,902,805 | 9/1975 | Redner | 356/116 |
| 3,927,947 | 12/1975 | Kasai | 356/117 |
| 3,988,067 | 10/1976 | Yamamoto et al. | 356/117 |

OTHER PUBLICATIONS

Redner S., "New Automatic Polariscope System"; *Experimental Mechanics* vol. 14, No. 12, Dec. 1974, pp. 486-491.

*Primary Examiner*—John K. Corbin
*Assistant Examiner*—R. A. Rosenberger
*Attorney, Agent, or Firm*—Stevens, Davis, Miller & Mosher

[57] ABSTRACT

This invention relates to a dynamic photoelasticimeter with a rotating birefringent element. It comprises a laser, a birefringent plate rotatable at a constant speed, a model to be studied, a circular analyzer and a photodetector supplying signals at its output having frequency components of $2\omega$ and $4\omega$. The ratio of the amplitudes of these signals supplies an indication of the phase shift $\phi(t)$ contributed by the model, and the phase of the signal of the frequency $4\omega$ contributes information as to the orientation $\theta$ of the axes of the model at the point in question.

The present invention provides a particularly simple and accurate dynamic photoelasticimeter.

5 Claims, 2 Drawing Figures

DYNAMIC PHOTOELASTICIMETER WITH ROTATING BIREFRINGENT ELEMENT

BACKGROUND OF THE INVENTION

This invention relates to a dynamic photoelasticimeter employing a rotating birefringent element.

Static photoelasticimeters which comprise rotating birefringent plates are described in copending U.S. patent application Ser. No. 835,004 filed Sept. 20, 1977. While the devices described in the aforesaid application permit study of a static model, the optical and electronic arrangements do not make it possible to carry out in a simple manner measurements in dynamic photoelasticimetry; that is, when the model to be studied is excited by shocks or by periodic vibrations.

The characteristic parameters at a given point of a birefringent model to be studied are the orientation $\theta$ of the fast axis of the point and the phase shift $\phi$ produced by the model between the light vectors moving along the fast axis and along the slow axis at the point. In the event the model to be studied is subjected to impacts or vibrations, these parameters $\theta$ and $\phi$ are functions of time.

In the following description, the letter $\omega$ is used either to designate frequencies or angular frequencies. The expression "birefringent" is used as a noun to designate an element which possesses birefringence (double refraction); for instance, a "rotating birefringent" may designate a mechanically turning doubly refracting plate or a Kerr cell subjected to a rotating field or the like.

SUMMARY OF THE INVENTION

An object of the present invention is to provide a dynamic photoelasticimeter employing a rotating birefringent which permits measurement of the birefringence characteristics of a model at a given point.

To achieve this object, the present invention provides a dynamic photoelasticimeter comprising a source of light such as a polarized laser. The beam of the laser strikes, in succession, against a birefringent turning at constant speed, a model to be studied subjected to a stress which is variable periodically or non-periodically in time, a circular analyzer and a photoreceiver. The signal produced at the output of the photoreceiver is filtered to obtain a $2\omega$ component containing information proportional to $\cos \phi$ and a $4\omega$ component containing information proportional to $\sin \phi$. After a suitable adjustment of the amplitudes of these signal, $\tan \phi$ can be determined from the ratio of the two amplitudes. The phase of the signal at the frequency $4\omega$ corresponds to the parameter $\theta$ or the tangent or cotangent of this parameter.

In accordance with a variant of the present invention, the source of light may be polychromatic and the measurements of the $2\omega$ and $4\omega$ components effected for several wavelengths.

BRIEF DESCRIPTION OF THE DRAWINGS

These objects and advantages, as well as other objects and advantages of the present invention, will become more evident from a reading of the following description, given with reference to the accompanying drawings, in which.

DESCRIPTION OF THE PREFERRED EMBODIMENTS

Figure 1:
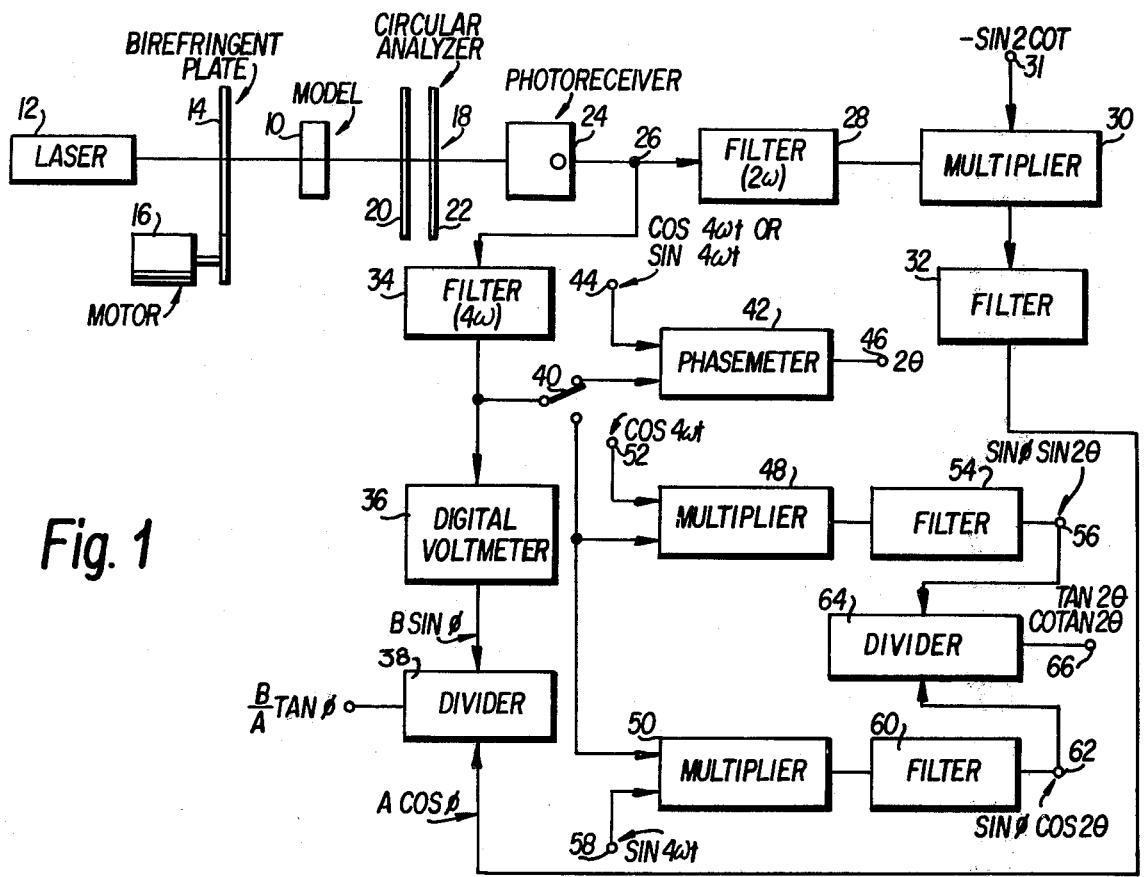
FIG. 1 shows schematically, in block form, a transmission photoelasticimeter in accordance with the present invention.

FIG. 1 illustrates a dynamic photoelasticimeter for measuring the parameters $\theta$ (t) and $\phi$ (t) of a transparent model 10 subjected to periodic shocks or vibrations. A source of light 12 consisting of a polarized laser is provided, the laser being polarized intrinsically or by the addition of a linear polarizer. The output beam of the laser then passes through a birefringent plate 14 rotated at a constant speed of angular frequency $\omega$ by a motor 16. The birefringent plate is characterized by a phase shift $\Phi$ which it contributes to light waves moving along its major axis and its minor axis respectively. The output beam of the laser next passes through the model 10 to be studied followed by a circular analyzer 18. Analyzer 18 is formed in conventional manner by the combination of a quarter-wave plate 20 and a linear polarizer 22, the quarter-wave plate having an angle of 45° with respect to the axes of the polarizer. The beam then reaches a photoreceiver 24 which provides an electrical signal at its output terminal 26.

The output signal obtained at the terminal 26 comprises a continuous component, a component having a frequency $2\omega$, and a component having a frequency $4\omega$. The $2\omega$ frequency component can be written $$E_2 = -(E_o/2) \sin \Phi \cos \phi \sin 2\omega t \tag{1}$$

The $4\omega$ frequency component can be written $$E_{4\omega} = (E_o/2) \cdot (1 - \cos \Phi) / \sin \phi \sin (4\omega t - 2\theta) \tag{2}$$

where $E_o$ designates the characteristic intensity of the source of light and of the absorption of the different optical elements.

$\Phi$ is a constant parameter specific to the rotating birefringent, $\phi$ and $\theta$ are the parameters of the model to be studied and which are functions of time, $\omega$ is the angular frequency of rotation of the rotating birefringent and t is time.

The ratio of the amplitudes of the signals $E_{4\omega}$ and $E_{2\omega}$ is proportional to $\tan \phi$, the coefficient of proportionality being dependent on the value of $\Phi$. This value can be measured; however, in an automatic apparatus it is preferable to provide a prior calibration of the apparatus by inserting a known birefringent of phase shift $\phi$ in place of the model to be studied.

With a birefringent having a known phase shift $\phi_c$ substituted for the model 10 of FIG. 1, the signal at output terminal 25 of photoreceiver 24 is coupled through a $2\omega$ band pass filter 28 to an input of a multiplier 30. In multiplier 30, the $2\omega$ output of filter 28 is multiplied by a reference signal $-\sin 2\omega t$ applied to terminal 31 thereby producing a signal at the output of a low pass filter 32 having a band width 0 to $\omega/5$ which is equal to A cos $\phi_c$. This is synchronous detection.

The signal at output terminal 26 of photoreceiver 24 is also coupled through a $4\omega$ band pass filter 34 to a digital voltmeter 36 which detects the amplitude of the 4ω signal and generates a signal equal to B sin $\phi_c$.

The signal at the output of voltmeter 36 is divided in a divider 38 by the output of filter 32 to obtain $$(B \sin \phi_c)/(A \cos \phi_c) = (B/A) \tan \phi_c.$$

Since tan $\phi_c$ is known, the gains of the component in the 2ω and 4ω paths can be adjusted until the output of divider 38 is equal to tan $\phi_c$ and A=B. When the birefringent having the known phase shift $\phi_c$ is replaced by a model 10 to be studied, the output of divider 38 will provide directly the tangent of the phase shift $\phi$ of the model. When the measurements are made by dynamic photoelasticimetry $\phi$ is a function of time, the model being excited by shocks or by vibrations.

The value of $\theta$ can be obtained in two ways:

(1) by a phase measurement between the 4ωt signal and a reference signal related to the rotation of the birefringent turning at constant speed, or (2) by multiplying the 4ωt signal by cos 4ωt and sin 4ωt respectively i.e. synchronous detection.

In the first method, the output of the 4ω filter 34 is coupled through a switch 40 to a phasemeter 42 having as a second input a reference signal applied to a terminal 44. When the phase of the reference signal, which may be either cos 4ωt or sin 4ωt, is compared in phasemeter 42 with the phase of the output of filter 34, an output corresponding to 2 $\theta$ is obtained at the output terminal 45 of the phasemeter. This first method is used when the birefringent model has a fixed axis, $\theta$ being obtained in numerical form.

In the second method, the output of the 4ω filter 34 is coupled through the switch 40 to multipliers 48 and 50. A reference input cos 4ωt at terminal 52 is applied to multiplier 48 and after multiplication with the output of filter 34 and transmission through filter 54 an output having a magnitude proportional to sin $\phi$ sin 2 $\theta$ is obtained at terminal 56. Similarly, a reference input sin 4ωt at terminal 58 is applied to multiplier 50 and, after multiplication with the output of filter 34 and transmission through filter 60, an output having a magnitude proportional to sin $\phi$ cos 2 $\theta$ is obtained at terminal 62. By dividing the signal at terminal 56 by that at terminal 62 in divider 64 an output signal corresponding to tan 2 $\theta$ is obtained at terminal 66. A signal corresponding to cotan 2 $\theta$ may also be obtained by dividing the signal at terminal 62 by that at terminal 56. This second method is used when the birefringent model has a movable axis, $\theta$ being obtained from tan 2 $\theta$ or cotan 2 $\theta$.

The manner of obtaining the cos 4ωt, sin 4ωt, cos 2ωt and sin 2ωt reference signals is well known and specific examples thereof are given in the aforementioned U.S. patent application Ser. No. 835,004.

Figure 2:
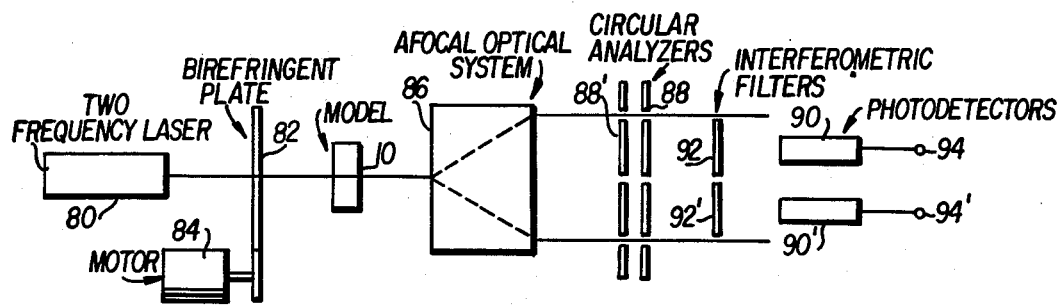
FIG. 2 shows schematically a transmission photoelasticimeter having several wavelengths, in accordance with the present invention.

The embodiment of the present invention described with reference to FIG. 1 makes possible the measurement of the parameter $\phi$ based on a trigonometric function of this parameter. Thus, the value of $\phi$ is determined to a precision of $\pi$. In the event the phase shift $\phi$ contributed by the model at the point studied is greater than $\pi$, the measurement becomes indeterminate. One method of removing this indeterminateness consists, as shown in FIG. 2, of using a laser 80 having two wavelengths $\lambda_1$ and $\lambda_2$. The laser beam passes through a birefringent plate 82 rotated at constant speed ω by motor 84, the model 10 to be studied and then through an afocal optical system 86 supplying a beam of large diameter. This large diameter beam is sent, via a first circular analyzer 88, towards a first photodetector 90 and via a second circular analyzer 88' towards a second photodetector 90'. Interferometric filters 92 and 94' having narrow pass-bands centered on the two wavelengths $\lambda_1$ and $\lambda_2$ of laser 80 make it possible to transmit to the photodetector 90 only the optical signals corresponding to the first wavelength $\lambda_1$ and to the photodetector 90' only the optical signals corresponding to the second wavelength $\lambda_2$. Based on these two measurements, one can, in known manner, as explained for instance in the aforementioned U.S. patent application Ser. No. 835,004 determine the phase shift $\phi$ contributed by the birefringent model 10 at the point in question, thereby removing the indeterminateness of $\pi$. The output terminals 94 and 94' of photodetectors 90 and 90' are coupled to means for filtering the 2ω and 4ω electrical signals at the outputs of the photodetectors 90 and 90' respectively and for detecting the phase and amplitude of the signal, as shown in FIG. 1.

We claim:

1. A dynamic photoelasticimeter for measuring as a function of time the birefringent parameters $\theta$ (t) and $\theta$ (t) of a model at a point subjected to stresses comprising, in succession
   a birefringent plate rotatable at a constant angular speed;
   a circular analyzer, said model being interposed between said birefringent plate and said circular analyzer;
   a photoelectric receiver;
   means for detecting the output signals from said photoelectric receiver at frequencies of 2ω and 4ω;
   means for determining the ratio of the amplitudes of said 2ω and 4ω output signals; and
   means for detecting the phase of said 4ω signal with respect to a reference frequency.

2. A dynamic photoelasticimeter for measuring as a function of time the birefringent parameters $\theta$ (t) and $\phi$ (t) of a model at a point subjected to stresses comprising, in succession
   a source of light emitting a light wave having at least two wavelengths $\lambda_1$ and $\lambda_2$;
   a birefringent rotatable at constant speed;
   said model;
   means for sending a first part of the light emerging from said model towards a first circular analyzer and a first photodetector, said first photodetector supplying a signal corresponding to the optical signals of wavelength $\lambda_1$;
   means for supplying another part of the light emerging from said model towards a second circular analyzer and a second photodetector, said second photodetector supplying a signal corresponding to the optical signals of wavelength $\lambda_2$;
   means for filtering the 2ω and 4ω signals at the outputs of said first and second photodetectors;
   means for measuring the output signal having a frequency of 2ω by synchronous detection means; and
   means for detecting the phase and amplitude of the 4ω signal.

3. A dynamic photoelasticimeter for measuring as a function of time the birefringent parameters $\theta$ (t) and $\phi$ (t) of a model at a point subjected to stresses comprising, in succession
   a source of light emitting a light wave having at least two wavelengths $\lambda_1$ and $\lambda_2$;
   a birefringent rotatable at constant speed;
   said model;

means for sending a first part of the light emerging from said model towards a first circular analyzer and a first photodetector, said first photodetector supplying a signal corresponding to the optical signals of wavelength $\lambda_1$;

means for supplying another part of the light emerging from said model towards a second circular analyzer and a second photodetector, said second photodetector supplying a signal corresponding to the optical signals of wavelength $\lambda_2$;

means for filtering the $2\omega$ and $4\omega$ signals at the outputs of said first and second photodetectors;

means for measuring the output signal having a frequency of $2\omega$ by synchronous detection means; and means for measuring the output signal having a frequency of $4\omega$ by synchronous detection means.

4. A dynamic photoelasticimeter according to claim 2, wherein the means for separating the optical beam into a first part and a second part is an afocal optical system.

5. A dynamic photoelasticimeter according to claim 3, where the means for separating the optical beam into a first part and a second part is an afocal optical system.

* * * * *